US006179583B1

United States Patent
Weston

(10) Patent No.: US 6,179,583 B1
(45) Date of Patent: Jan. 30, 2001

(54) METERED FLUID DELIVERY DEVICE

(75) Inventor: Terence Edward Weston, Suffolk (GB)

(73) Assignee: Weston Medical Limited, Suffolk (GB)

( * ) Notice: Under 35 U.S.C. 154(b), the term of this patent shall be extended for 0 days.

(21) Appl. No.: 09/376,947

(22) Filed: Aug. 18, 1999

Related U.S. Application Data

(63) Continuation-in-part of application No. PCT/GB98/00491, filed on Feb. 17, 1998.

(30) Foreign Application Priority Data

Feb. 25, 1997 (GB) .................................................. 9703918
Aug. 19, 1998 (GB) .................................................. 9818111

(51) Int. Cl.$^7$ .............................. F04B 17/00; F04B 19/02
(52) U.S. Cl. ........................... 417/392; 417/462; 417/464; 222/334; 222/386.5; 604/152
(58) Field of Search ............................. 222/95, 334, 368, 222/386.5; 417/234, 411, 392, 462, 464, 465; 604/152; 91/503

(56) References Cited

U.S. PATENT DOCUMENTS

| | | | |
|---|---|---|---|
| 920,201 | * 5/1909 | Sleeper | 417/462 |
| 1,388,997 | * 7/1921 | Pease | 417/392 |
| 3,056,356 | * 10/1962 | Piper | 417/462 |
| 3,294,032 | * 12/1966 | Sundblom | 417/462 |
| 3,731,679 | * 5/1973 | Wilhelmson et al. | 417/411 |
| 4,773,565 | 9/1988 | Rohlfing | 222/145 |
| 5,368,195 | 11/1994 | Pleet et al. | 222/52 |
| 5,547,110 | 8/1996 | Keller et al. | 222/219 |

FOREIGN PATENT DOCUMENTS

| | | |
|---|---|---|
| 0406800 | 1/1991 | (EP) . |
| 646776 A1 | 4/1995 | (EP) . |
| 233004 | 5/1925 | (GB) . |
| 852299 | 10/1960 | (GB) . |
| 1091215 | 11/1967 | (GB) . |
| 1198736 | 7/1970 | (GB) . |
| 2025379 | 1/1980 | (GB) . |
| 93/04714 A1 | 3/1993 | (WO) . |
| 98/38480 A1 | 9/1998 | (WO) . |

\* cited by examiner

*Primary Examiner*—Charles G. Freay
(74) *Attorney, Agent, or Firm*—Darby & Darby

(57) ABSTRACT

A metering device for pressurized fluids has a rotor containing an oscillating free piston operating in a bore at right angles to the rotor axis. The piston is driven by the fluid to be metered. The rotor is retained within a stator having inlet and outlet ports. When the rotor is rotated, a first end of the bore becomes in fluid connection with the inlet port and the piston is operated upon by the pressurized fluid and moves within the bore in a first direction towards the outlet port. As the rotor is turned further, the second end of the bore becomes in fluid connection with the inlet port whilst the first end is made in fluid connection with the outlet port, and the piston reverses to move in a second direction, i.e. towards the outlet port to discharge the fluid which had previously moved the piston in a first direction. The rotor may be turned back and forth to dispense metered doses of the fluid, or may be rotated continuously or intermittently in the same direction to dispense metered doses of the fluid.

12 Claims, 5 Drawing Sheets

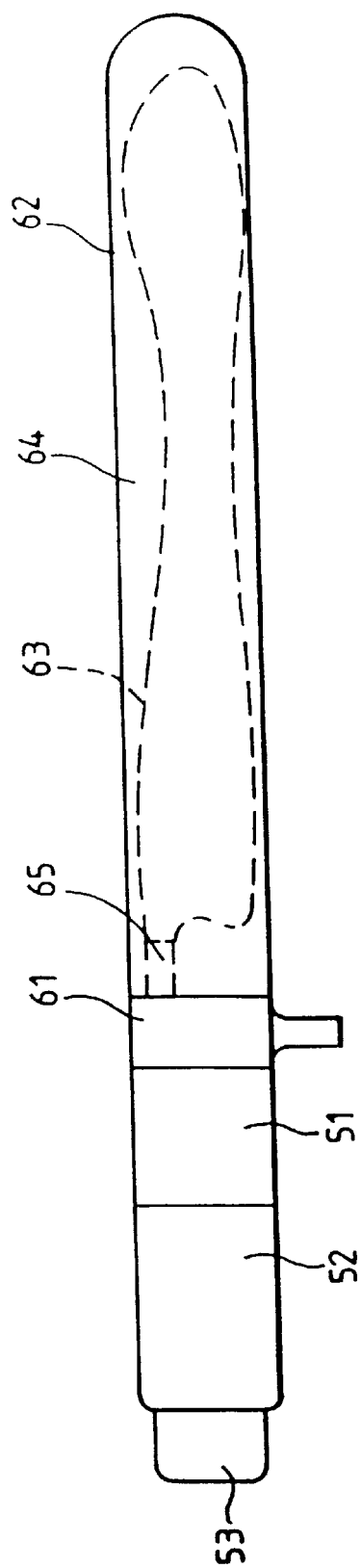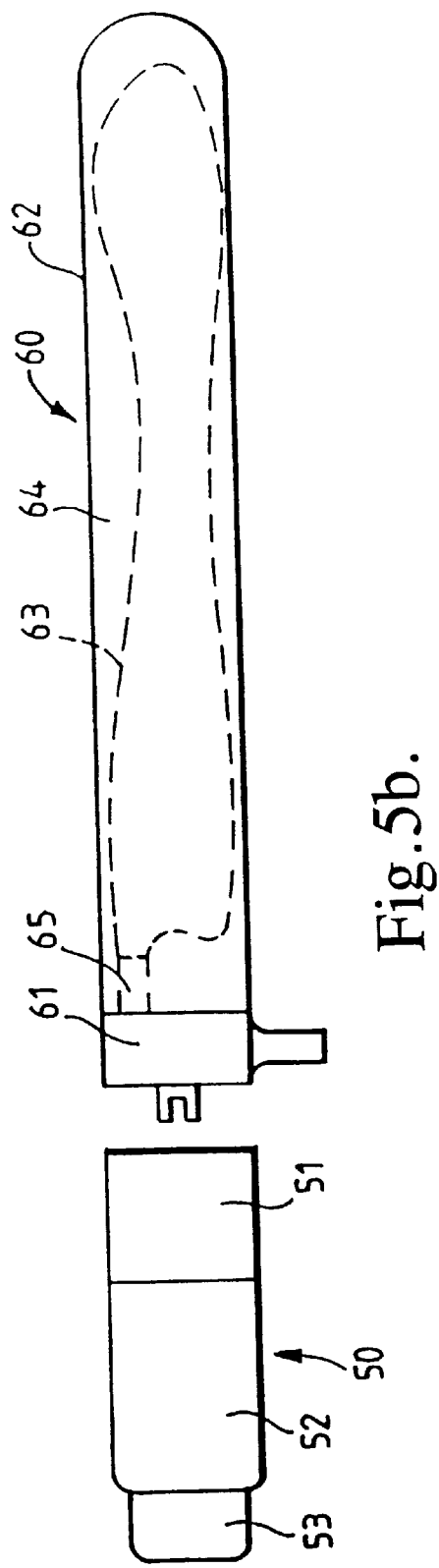
Fig.5a.
Fig.5b.

METERED FLUID DELIVERY DEVICE

CROSS REFERENCE TO RELATED APPLICATION

This application is a continuation-in-part of International Application PCT/GB98/00491, filed Feb. 17, 1998, and designating the United States of America. The entire disclosure of the aforesaid international application is incorporated herein by reference.

FIELD OF THE INVENTION

This invention relates to a device having a fluid metering device, for example a medical device for metered flow delivery to a patient. Fluid metering devices are among the oldest and most diverse of man's inventions. The main types are positive displacement dispensers, as used in fuel injection systems; fixed or variable restrictors which control the flow rate of pressurised fluids—e.g. needle valves; automatic cisterns which discharge a predetermined quantity of water once a certain level is reached; and, often, metering combined with pumping, as with peristaltic pumps.

BACKGROUND OF THE INVENTION

Metering devices are used extensively in the health care industry. Typical of the applications are syringe pumps for delivering medicaments directly into the patient's bloodstream, wherein a stepper motor drives a lead screw to move the plunger of the syringe to dispense the medicament. The metering is accomplished by controlling the motor speed and hence the frequency of plunger travel. These syringe pumps suffer a number of drawbacks; they are relatively expensive; the dosage accuracy depends on the diameter of the plunger, which may vary with different manufacturers; particularly at low flow rates the plunger can suffer from stiction, which causes variations in the delivery rate; and a drive signal to the stepper motor does not always result in movement of the motor shaft if there is significant resistance to flow. On the positive side, they are easy to set up and maintain, fairly reliable, and generally convenient to use.

Another type of metering pump used extensively in hospitals and for ambulatory drug delivery devices is the peristaltic pump. This consists of an elastomeric tube containing a fluid, one end of the tube being connected to a reservoir of the fluid to be pumped, and at least one pair of rollers spaced apart which are pressed onto the tube to trap a bolus of fluid therein, and which traverse along the tube to move the bolus towards an outlet. Such pumps employ a number of rollers around a drum or on a linear track, so that there is a slightly intermittent delivery rate of fluid as each bolus is delivered. The intake suction is created by the tube springing out after the passage of a roller. Peristaltic pumps deliver a reasonably accurate flow when the pump tubes are new, but the tube material quickly loses some of its elasticity and the flow rate drops. Furthermore, it is quite common for tubes to split unless changed frequently. The good features are that they are simple to set up and maintain; no glands or sliding seals are required; the tubes are often contained conveniently within a disposable cartridge, including the rollers; they are relatively inexpensive.

Another metering device used very commonly in hospitals is the very simple drip controller which is used in conjunction with intravenous infusion sets. The basic device consists of a clamp which is adjusted to partially occlude a resilient tube leading from the infusion drug container. The flow rate is determined by counting the drops within a viewing chamber; some equipment monitors the drip rate electronically. They are less complicated than pumps, and the fluid is pressurised by fixing the container above the delivery level. They have no moving parts, and few maintenance problems. However, because of changes in the pressure head as the infusion drug is consumed, the flow rate falls, and such controllers require frequent adjustment. Although various types of tube clamps are in use, inevitably the soft tubing material creeps after the initial setting, necessitating further adjustment. Also they present difficulties when used with viscous solutions. More sophisticated controllers use feedback to control the variable restrictor, but there are few, if any, suitable flow measuring devices that can cover the range of flow rates required with accuracy, at a reasonable cost.

With the first two examples, the pump could build up a pressure on the delivery side if a blockage occurs, and a pressure warning device is essential. In the last example of a metering device, a blockage downstream would merely cause the flow to cease, but again, an alarm is essential.

Another metering device used for drugs is the metered dose inhaler (MDI) which is used to deliver successive doses of drugs in a spray of fine droplets having a mean diameter of about 5 microns. Generally the device contains a drug mixed with a liquefied gas propellant; a metered volume of the mixture is first isolated from the bulk, and then opened to atmosphere, whereupon the propellant boils almost explosively and dissipates the drug as a fine spray. Until recently such MDI's relied entirely on the use of CFC's as the propellant, but with the alleged ozone depletion caused by such chemicals, new ways have been found to power MDI's, such as the device co-invented by the present inventor, described in WO 91/14468, which employs very high pressure to atomise the metered dose of drug. However, this device is bulky compared to propellant MDI's, since it employs a spring-loaded piston which must be compressed, latched, and released on demand to dispense the dose.

In addition to the clamp type controller discussed, other types are needle valves, which are viscosity sensitive and suffer from particulate contamination which increases flow resistance, and flow interrupts such variable frequency on-off valves, which are very viscosity sensitive.

Hence it may be seen that there are two basic ways of metering medical fluids: by flow rate control of pressurized fluids, as in the tubing clamp on IV infusion sets, and by positive displacement pumps, such as syringe pumps. The former are usually inexpensive and inaccurate, the latter just the opposite. Generally it is simple and inexpensive to pressurize fluids, for example by storing them in a container with compressed gas, or by placing a weight onto a closed bag of fluid. However, to the present inventor's knowledge, none of the flow control elements currently available have sufficient accuracy and/or stability to give accurate dispensing over a wide range of delivery rates.

These problems may be overcome by introducing feedback, so that the delivered flow rate is compared with a set value, and the controlling element adjusted accordingly. The resulting devices are more complex, larger, expensive, and generally unsuitable for small flow rates. For many applications, the fundamental problem is that there are no accurate flow measuring devices which are capable of a wide dynamic range, suitable for a wide range of viscosities, and costing very little to manufacture. Among methods in use today are impellers which are placed in the fluid stream and rotate according to the flow rate; Doppler effect devices;

and thermal, ultrasonic, optical, and gravimetric instruments. Most have serious drawbacks, such as sensitivity to viscosity, density, change from laminar to turbulent flow, a variable velocity profile within the measuring conduit, and environmental change. Tremendous advances in metrology science have enabled all of these problems to be solved for particular applications, but always at the expense of limited range or difficult fluid conditioning requirements such as ultra filtration.

It is recognised that there never will be one solution for the infinite variety of fluid metering requirements, but nevertheless there is still scope for significant advance in the art.

SUMMARY OF THE INVENTION

In one aspect the present invention seeks to overcome some of the drawbacks of existing metering devices by providing a fluid metering dispenser for use with pressurized fluids, having a rotor containing a piston free to oscillate within a bore extending transversely to the rotor axis, and which piston is driven by the fluid to be metered. Preferably, the rotor is sealingly retained within a stator having an inlet port connected to a pressurised fluid source, and an outlet port. When the rotor is rotated, a first end of the bore becomes in fluid connection with the inlet port of the stator, and the piston is urged by the pressurized fluid to move in a first direction towards the outlet port. As the rotor is turned further, the second end of the bore becomes in fluid connection with the inlet port, whilst the first end of the bore becomes in fluid connection with the outlet port, and the piston, again urged by the fluid, reverses to move in a second direction, i.e. towards the outlet port; thus the fluid which previously had moved the piston in a first direction is discharged through the outlet port. The rotor may be turned back and forth to dispense successive metered doses of fluid, or may be rotated in the same direction continuously or intermittently for a similar result. Thus a motorised version will deliver accurate metered quantities of fluid as the rotor rotates and the piston oscillates. Clearly there must be sufficient pressure to move the piston for its full stroke within the time allowed by the rotational speed of the rotor, but a wide operating range is possible. For low pressure applications, the piston may have a small clearance within the bore, to reduce the friction losses to a very small amount, and the mass may be small to minimise inertial losses.

In another aspect the present invention seeks primarily to overcome some of the drawbacks of existing medical devices for metered fluid delivery to a patient by providing a fluid metering dispenser for use with pressurized fluids, having a rotor containing a piston free to oscillate within a bore extending transversely to the rotor axis, and which piston is driven by the fluid to be metered. Preferably, the rotor is sealingly retained within a stator having an inlet port connected to a pressurised fluid source, and an outlet port. As the rotor is rotated it moves between a position in which a first end of the bore is in fluid connection with the inlet port of the stator, and a second end is in fluid communication with the outlet port, and a position in which the first end is connected to the outlet port and the second end is connected to the inlet port. The rotor may be turned back and forth to dispense successive metered doses of fluid, or may be rotated in the same direction continuously or intermittently for a similar result. Thus a motorised version will deliver accurate metered quantities of fluid as the rotor rotates and the piston oscillates. Clearly there must be sufficient pressure to move the piston for its full stroke within the time allowed by the rotational speed of the rotor, but a wide operating range is possible. For low pressure applications, the piston may have a small clearance within the bore, to reduce the friction losses to a very small amount, and the mass may be small to minimise inertial losses.

In one embodiment thereof the invention provides an ambulatory or non-ambulatory, medical pump which is provided with such a metering device, the pressurised fluid source preferably being of the bag-in-the-can type (see below). In another embodiment the invention provides a medical infusion pump with such a metering device, the pressure for the fluid source preferably being provided by gravity.

The rotor may be operated manually or by a motor, which includes various electric, air, clockwork, hydraulic and gravimetric types. It is intended that for some applications, such as IV infusion, the metering element is to be disposable. The main benefits are that there will be no need to clean and sterilize the device, the duty cycle of the metering element is very short, which enables low-cost manufacture, and the more expensive parts such as the drive unit are retained for use with a fresh metering element.

Detector s may be fitted to measure the piston frequency and/or position and operate an alarm or flow rate display in dependence thereon. Again, the enhancement may be part of the drive unit, so keeping the metering element simple and inexpensive. For structural reasons, it may be preferred that roles of the stator and rotor are reversed—that is, the piston oscillates within a cylindrical stator, whilst the rotor rotates around the outside of the cylinder.

A first preferred embodiment provides a short cylindrical rotor having a cylindrical bore at right angles to, and passing through, the axis of rotation of the rotor. A piston is located within the bore and has a running clearance sufficiently small to prevent leakage of the fluid to be metered. (This clearance may vary according to the viscosity and pressure of the fluid). Each end of the cross bore may be connected to a respective circumference groove. The grooves are not connected together, and serve as distribution channels for the fluid. The rotor is sealingly retained within a stator, which has inlet and outlet ports aligned to connect to the distribution grooves, if present. As the rotor is rotated, the distribution grooves, if present, connect alternately with the inlet and outlet ports of the stator, and thus each end of the cross bore in the rotor is alternately presented to the pressure inlet port. This results in the piston oscillating within the cross bore, and discharging the swept volume fluid content of the bore through the outlet port of the stator. The rotor is driven by a motor and gearbox, and is releasably attached to the metering dispenser, so that the latter may be replaced easily. To avoid contamination of the fluid, the rotor and stator are not lubricated, and the materials of construction are chosen to minimise friction and be compatible with the fluid and application. The motor is fitted with a speed controller, by which means the output of the metering dispenser may be altered.

A second preferred embodiment provides a similar device to the first, except that it is adapted to work at high pressures. The rotor is of frusto-conical form and mates with a similar form within the stator. The rotor is biassed by a spring to ensure sealing contact between the two at pressures of up to 500 bars. Because of the higher pressure, the piston is sealingly fitted within the cross bore, or has a very small running clearance that will prevent significant leakage between the piston and bore. Because of the high contact forces between the rotor and stator, the materials of each are suitable for dry friction without a lubricant, although certain lubricants such as molybdenum disulphide may be used if the inevitable contamination of the fluid by the lubricant is permissible.

BRIEF DESCRIPTION OF THE DRAWINGS

The detailed description of the invention refers to the following drawings:

FIGS. 1a, 1b and 1c show different views of a first embodiment, FIG. 1a being a plan view, and FIGS. 1b and 1c being sectional views along lines B—B and C—C, respectively, shown in FIG. 1a;

FIG. 5a shows an assembled ambulatory pump incorporating the invention;

FIG. 5b shows an ambulatory pump shown in FIG. 5a with the power pack and the meter device portion separated.

DETAILED DESCRIPTION OF THE INVENTION

Figure 1A:
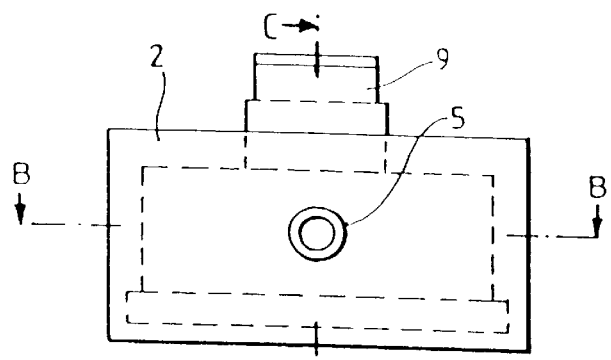
Figure 1B:
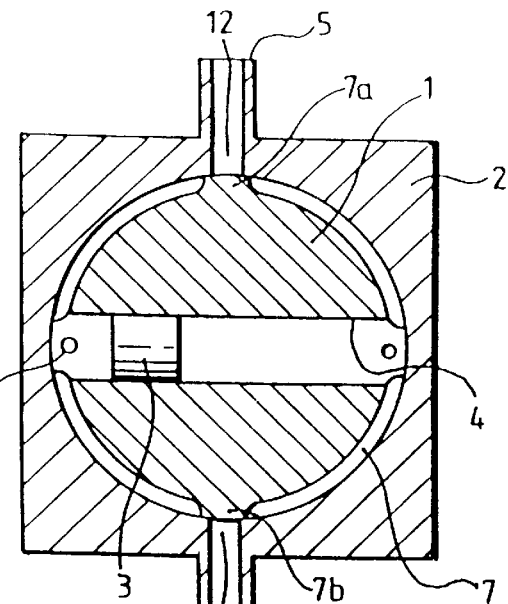
Figure 1C:
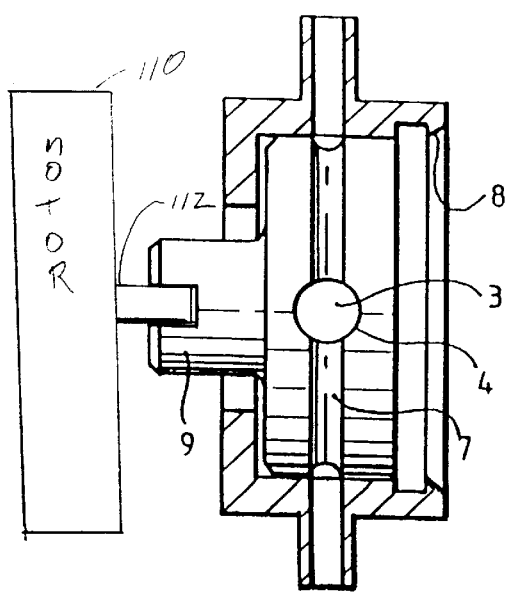

FIGS. 1a to 1c show a stator 2 defining a cavity therein and having connectors 6 and 5, and a rotor 1 with a transverse bore 4, at right angles to the axis of rotation of the rotor 1, containing a piston 3. The rotor has a drive shaft 9 connected thereto. A motor 110 having a drive shaft 112 connects to the shaft 9 to drive the same. The rotor is circular in cross-section, and in the embodiment of FIGS. 1a to 1c it is generally cylindrical. Each end of the bore 4 is in fluid connection with distribution grooves 7, forming fluid chambers, in the periphery of the rotor 1. Stator 2 has an outlet port 12 terminating with the connector 5, and an inlet port 11 terminating with the connector 6. (Note that in the configuration shown, the ports are interchangeable as regards function). Piston 3 is a small clearance fit within bore 4, so that the fluid will not leak through the capillary annulus, and the piston 3 may optionally be limited by stop pins 10 inserted in the rotor 1 after assembly of the piston 3. Alternatively, the piston may be stopped by coming to rest against the stator 2. Where pins 10 are fitted, they may be used to trigger timing circuits and alarms etc. Referring to FIG. 1c, rotor 1 is retained within stator 2 by a retaining lip 8, and drive shaft 9 is suitably adapted to fit a plug-in drive means, not shown. Preferably, rotor 1 is made from a transparent material such as polymethylmethacrylate or similar hard plastic, and stator 2 is made from a low friction resilient plastic material such as PTFE or polypropylene. For low pressures, a slight interference fit of the rotor 1 in stator 2 is sufficient to act as a rotary seal, but higher pressures may require separate low friction seals.

Figure 3A:
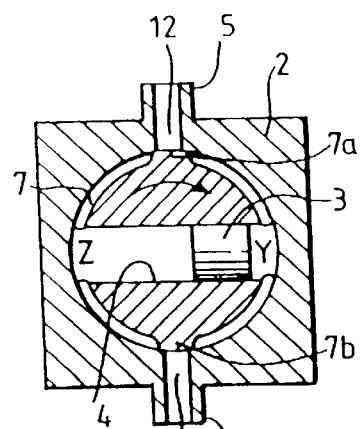
FIGS. 3a, 3b and 3c illustrate the operating sequence of the metering dispenser.
Figure 3B:
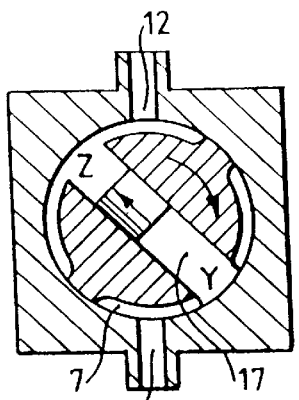
Figure 3C:
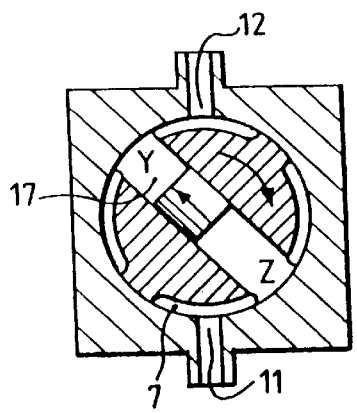

Referring now to FIG. 3a, inlet port 6 is connected to a source of pressurized fluid, and rotor 1 is shown in one extreme stroke position: the volume of bore 4 to the left of piston 3 as seen in FIG. 3a contains only air, and ports 11 and 12 are blocked by respective lands 7a and 7b which separate the grooves 7 from one another. When the rotor 1 is rotated clockwise, (See FIG. 3b) the end Y of bore 4 connects to inlet port 11 via one of the grooves 7. The pressurized fluid 17 on the side of the piston leading to the Y end of the bore 4 urges piston 3 along bore 4 in the direction of the Z end of the bore 4, and the air in front of the piston is expelled through the other groove 7 and port 12. Further rotation of rotor 1 to the position of FIG. 3c causes fluid to enter the bore at the Z end thereof, so that piston 3 travels in the opposite direction to expel the fluid 17 through port 12 via groove 7. Of course the rotor 1 may be turned continuously, which will result in the delivery of a continuous succession of metered doses of fluid 17 at a rate determined by the rotational speed of rotor 1. Thus it may be seen that the fluid that first acted on the piston 3 to displace the piston becomes the fluid acted upon by the piston 3. Provided there is sufficient fluid pressure to complete each piston stroke (twice each revolution), within the time available (which will depend on the rotational speed of the rotor), the device will deliver very accurate metered doses. As an alternative to continuous rotation, the rotor may oscillate back and forth, for example through 180°.

Figure 2:
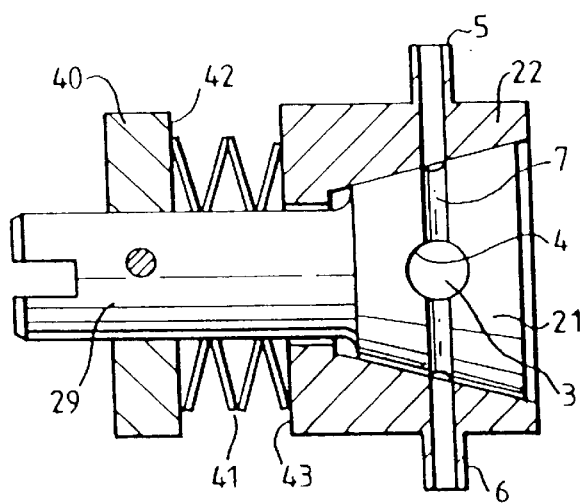
FIG. 2 shows a high pressure version, as provided by a second embodiment.

Referring now to FIG. 2, this shows a similar device to that shown in FIG. 1, but using a frusto-conical rotor 21 sealingly and rotatably assembled into stator 22. Rotor 21 has a shaft 29, fitted with a collar 40. A stack of disc springs 41 in compression acts on face 42 of collar 40 and reacts against thrust face 43 of stator 22 to bias the conical surface of rotor 21 sealingly against the corresponding conical surface of stator 22. The metering dispenser is operated as previously described. Because high contact forces are produced on the conical surfaces, suitable materials may be selected to give good sealing and compatibility with the fluid being dispensed. Typically, a rotor may be made from graphite or modified PTFE, and the stator from stainless steel.

Figure 4:
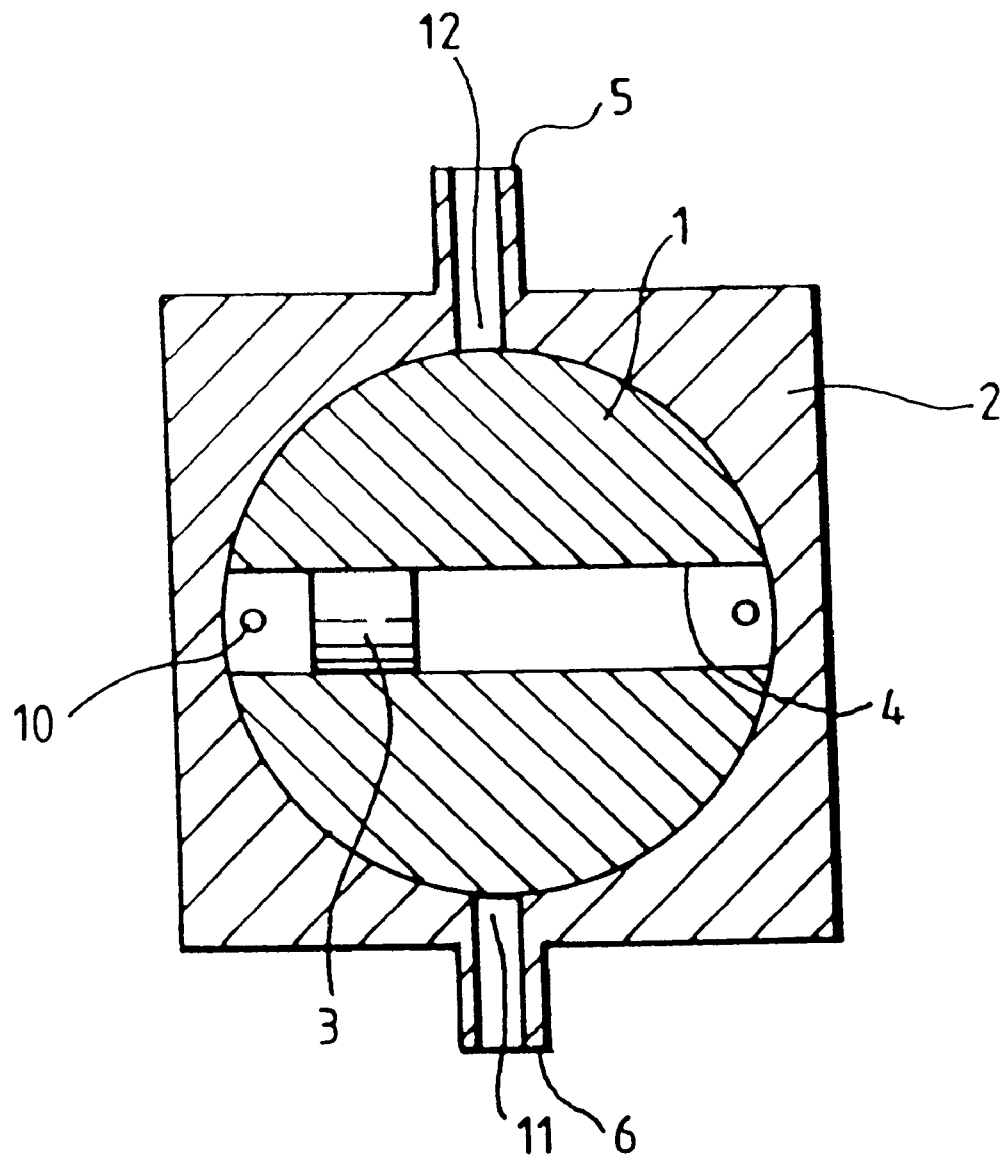
FIG. 4 is a view, similar to FIG. 1b, but showing a further embodiment.

The embodiment shown in FIG. 4 differs from that shown in FIGS. 1a to 1c solely in that the grooves 7, and therefore the lands 7a and 7b are omitted. This means that fluid can only enter and leave the bore 4 when the ends of the bore are aligned with the ports 11 and 12. It will be understood that the same modification may be made to the embodiment of FIG. 2.

Where the device is to operate at low pressure it is sufficient that the piston should have a small clearance in the bore (typically about 0.1% of the diameter). For higher pressures, seals, for example lip seals or 'O' rings, and/or lubricants may be required.

The metering device may be integral with, or permanently secured to (e.g. by crimping), or removably connected to, a pressurized container of a fluid, e.g. a medical fluid, or a container of fluid, e.g. a medical fluid, which is subsequently pressurized. A simple example of the latter is an IV infusion bag containing the liquid to be metered: it does not have a working pressure until it is lifted to a height above the patient onto a support stand, or placed into a holder and compressed with a weight or spring. Alternatively the metering device may be inserted into a pressurized pipeline for a wide range of metering applications, e.g. medical applications. One application where the metering device of the present invention may be of particular value is for metering fluid from a so-called "bag-in-can" dispensing system. This is a system in which a fluid, e.g. a cream for toiletry purposes, but potentially any fluid (for example a pharmaceutical material), is held in a flexible bag which is located inside a can. The can contains a substance for pressurising the interior itself, e.g. butane in liquid form, or a compressed permanent gas such as nitrogen, whereby to exert a dispensing pressure on the bag when the outlet from the bag to the exterior is opened.

FIG. 5 shows an ambulatory pump incorporating the present invention. It will be seen that this consists of two units. One is a power pack 50 comprising an electric motor 51, a battery 52 to provide power to the motor, and a controller 53 for varying the speed of the motor and therefore the dose rate of the pump. The other unit 60 comprises a metering device 61 as already described and a gas-pressurised bag-in-the-can dispenser 62. The collapsible bag 63 contains the fluid to be dispensed, and the region within the outer can and around the bag contains pressurised gas. The bag is connected to the metering device by a connector 65. After use, the unit comprising the dispenser and the metering device can be discarded, and a fresh unit fitted to the power pack. Alternatively, both may be discarded, in which case there is no need to be able to disconnect one from the other.

Instead of the bag-in-the-can technology some other form of pressurisation could be used, for example a spring-powered syringe or a rubber balloon. This latter device is known for use with aerosols, and is basically a thick-walled elastomeric balloon which is inflated by the liquid product itself (no gas is used). The balloon exerts a more or less constant pressure on the liquid inside, so that when an outlet valve is opened the product is dispensed.

It should also be noted that although FIG. 5 shows a pump which is intended to be ambulatory, the same principles could be employed in a non-ambulatory version, for example one intended for a bedside version.

Figure 6A:
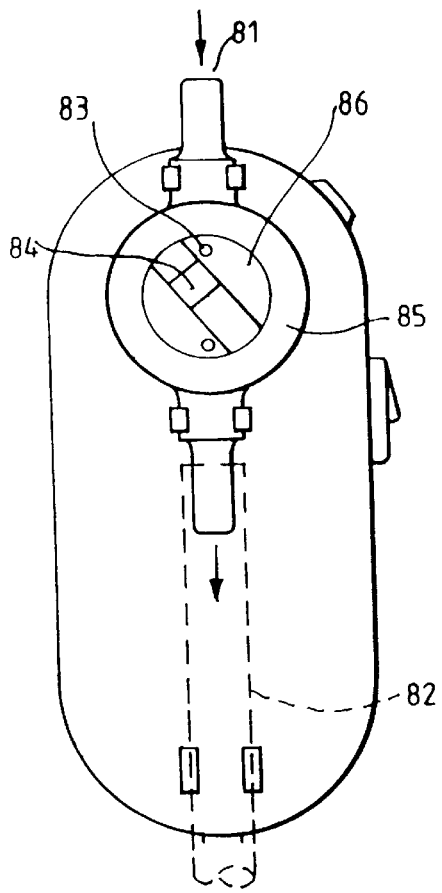
FIGS. 6a and 6b shows an infusion device incorporating the invention.
Figure 6B:
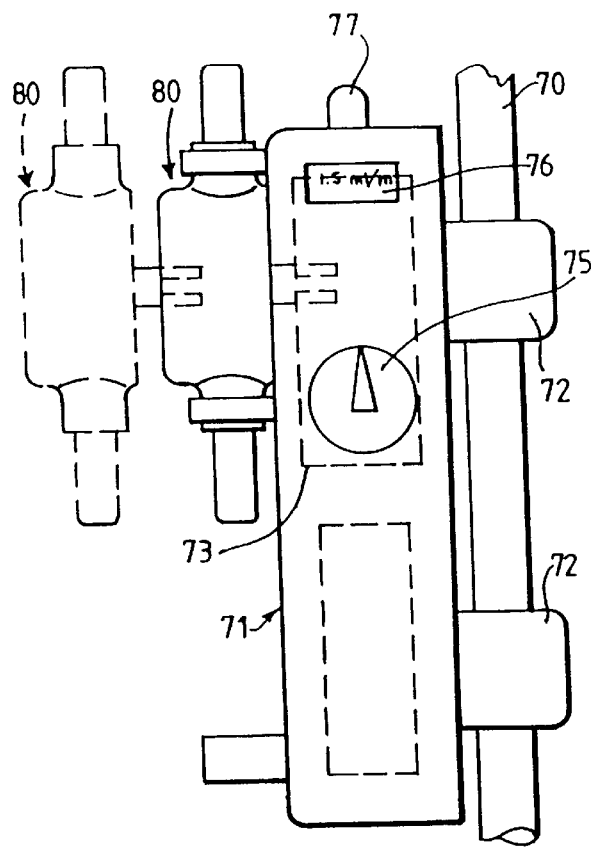

FIGS. 6a and 6b show an infusion device. This comprises a support pole 70 on which a motor unit 71 is mounted by retaining brackets 72 for adjustment up and down the pole. The motor unit comprises an electric motor 73, a battery 74 to provide power to the motor, and a controller for varying the speed of the motor and thus the flowrate. The drawings shows a lockable flowrate controller 75, a display 76 for displaying the flowrate and a status indicator 77. A second unit 80 is removably clipped to the motor unit and comprises a metering device 85 as already described. This meters fluid from a pressurised fluid input 81 to a fluid output 82 which is connected to a patient. The drawing shows detectors 83 for detecting the position 84 within the rotor 86 of the piston of the metering device. These can be used to detect completion of each dispensing cycle. In conjunction with other detectors, e.g. refractive index sensing devices, for detecting the presence or absence of liquid in the metering device, these can be used to operate suitable alarms, for example audible, visible, or both, to indicate a malfunction. The ambulatory pump described above could also incorporate such alarms.

In operation, the device would first be run, preferably at high speed, without being connected to the patient, to purge the pipework of air, and only then connected to the patient.

Although FIGS. 5 and 6 show electric motors, it is to be understood that other motors, for example other motors of the types already mentioned above, could be used instead. Indeed, under some circumstances no motor might be used, the device being moved by human power. Although this would not generally be appropriate in the context of a device for dispensing medical products, a manually powered dispenser might be entirely appropriate to dispense other products, for example toothpaste, hand creams and industrial products, and such dispensing devices are within the scope of the present invention.

What is claimed is:

1. A fluid metering device which comprises a stator, have an internal wall defining a cavity therein, a rotor mounted in said cavity, and defining, with said internal wall, at least and a first and a second fluid chamber, a bore extending through the rotor from the first fluid chamber to the second fluid chamber, a piston movable along the bore and defining first and second bore regions on either side thereof, a fluid inlet port for supplying fluid to the cavity, a fluid outlet port for receiving fluid from the cavity, the rotor being rotatable with respect to the stator about an axis of rotation between a first position in which the fluid inlet port communicates via the first chamber with the first bore region and the fluid outlet port communicates via the second chamber with the second bore region, and a second position in which the fluid inlet port communicates via the second chamber with the second bore region and the fluid outlet port communicates via the first chamber with the first bore region, said device further comprising stop means for limiting the extent of range of the piston along the bore.

2. A device according to claim 1, further comprising a motor for providing rotation of the rotor.

3. A device according to claim 1, arranged for continuous rotation of the rotor in the same direction.

4. A device according to claim 1, arranged for oscillating rotation of the rotor.

5. A device according to claim 1, wherein the first and second chambers are provided by respective grooves formed in the rotor and are separated from one another by lands.

6. A device according to claim 1, wherein the rotor is generally circular in cross section, and the bore therein extends at right angles to the longitudinal axis thereof.

7. A device according to claim 6, wherein the rotor is generally cylindrical.

8. A device according to claim 6, wherein said rotor is frustoconical and has a frustoconical wall adjacent said internal wall of said stator.

9. A device according to claim 8, comprising spring means for urging the frustoconical wall of the rotor into fluid sealing engagement with said internal wall of said stator.

10. A fluid dispensing system comprising a fluid metering device according to claim 1, and a source of fluid connected to the fluid inlet port of the metering device.

11. A system according to claim 10, wherein the source of fluid comprises a fluid-containing bag held within a container which is pressurisable to exert a dispensing pressure on the bag.

12. A medical infusion device comprising a fluid inlet for connection to a source of infusion fluid; a fluid outlet for connection to a patient; and a fluid metering device which comprises a first member having an internal wall defining a cavity therein, a second member mounted in said cavity, and having a bore extending therethrough, a piston movable along the bore and defining first and second bore regions on either side thereof, a fluid inlet port, connected to said fluid outlet, for receiving fluid from the cavity, the first and second members being rotatable with respect to one another about an axis of rotation between a first position in which the fluid inlet port communicates with the first bore region and the fluid outlet port communicates with the second bore region, and a second position in which the fluid inlet port communicates with the second bore region, and a second position in which the fluid inlet port communicates with the second bore region and the fluid outlet port communicates with the first bore region, said device comprising a stand, and the means for adjusting the vertical position of the remainder of the device on the stand, said device comprising a first unit mounted on the stand and including a display means, and a second unit removably connected to the first unit and including the said fluid metering device.

* * * * *